United States Patent [19]

Schroeder

[11] Patent Number: 4,833,269

[45] Date of Patent: May 23, 1989

[54] METHOD FOR PURIFYING TEREPHTHALIC ACID RECYCLE STREAMS

[75] Inventor: Hobe Schroeder, Warrenville, Ill.

[73] Assignee: Amoco Corporation, Chicago, Ill.

[21] Appl. No.: 228,995

[22] Filed: Aug. 5, 1988

[51] Int. Cl.$^4$ ............................................ C07C 51/487
[52] U.S. Cl. .................................... 562/484; 562/414; 562/486
[58] Field of Search .......................... 562/414, 487, 486

[56] References Cited

U.S. PATENT DOCUMENTS 4,467,110  8/1984  Puskas et al. ........................ 562/487

Primary Examiner—Werren B. Lone
Assistant Examiner—Vera C. Clarke
Attorney, Agent, or Firm—Gunar J. Blumberg; William H. Magidson; Ralph C. Medhurst

[57] ABSTRACT

A process is disclosed for purifying a crude terephthalic acid mother liquor stream comprising oxidation catalysts, terephthalic acid, color bodies and impurities by hydrogenation in the presence of a rhodium-on-carbon catalyst wherein color bodies and impurities are hydrogenated to saturated compounds for subsequent oxidation to carbon oxides. The terephthalic acid in said stream is thereupon recovered.

4 Claims, No Drawings

METHOD FOR PURIFYING TEREPHTHALIC ACID RECYCLE STREAMS

FIELD OF THE INVENTION

This invention relates to a method for purifying terephthalic acid recycle streams, recovery of terehhthalic acid (TA) and oxidation of high molecular weight impurities in a highly acid mother liquor in a process wherein terephthalic acid is manufactured by oxidation of paraxylene. This invention permits the recycle of mother liquor from the oxidation process, thus conserving acetic acid and catalyst, without affecting the optical quality of terephthalic acid product. This invention permits the recovery of product from the oxidation process, which product would otherwise be discarded in the acidic effluent stream with high molecular weight impurities produced in the oxidation process. The invention is also applicable to recovery of product of other polycarboxylic acids such as trimesic, isophthalic, naphthalene dicarboxylic, trimellitic, mellitic, etc., produced by oxidation of precursors.

BACKGROUND OF THIS INVENTION

Polymer grade or "purified" terephthalic acid is the starting material for polyethylene terephthalate, which is the principal polymer for polyester fibers, polyester films, and resins for bottles and like containers. Polyester fibers are used in textiles as well as in industrial applications such as tire cord. Polyester films coated with adhesives and emulsions are useful as wrapping tapes, photographic films, recording tapes, and the like.

Purified terephthalic acid is derived from relatively less pure, technical grade or "crude" terephthalic acid by purification of the latter utilizing hydrogen and a noble metal catalyst as described in U.S. Pat. No. 3,584,039 to Meyer. In the purification process, the impure terephthalic acid is dissolved in water at an elevated temperature, and the resulting solution is hydrogenated, preferably in the presence of a hydrogenation catalyst, e.g., palladium on a carbon support, as described in U.S. Pat. No. 3,726,915 to Pohlmann. This hydrogenation step also converts the various color bodies present in the relatively impure terephthalic acid. Another related purification-by-hydrogenation process for aromatic polycarboxylic acids produced by liquid phase catalyst oxidation of polyalkyl aromatic hydrocarbons is described in U.S. Pat. No. 4,405,809 to Stech et al.

Terephthalic acid impurities are of several types. The compound 4-carboxybenzaldehyde (4-CBA), an intermediate product in the oxidation of para-xylene, is found in impure terephthalic acid. Color-forming precursors and color bodies of the benzil, fluorenone or anthraquinone structure, are usually present. Nitro-compounds are found as impurities in terephthalic acid obtained by liquid phase nitric acid oxidation of para-xylene and other suitable starting materials. All of these impurities are deleterious with respect to polyester quality. Any method of purifying crude terephthalic acid to produce fiber-grade terephthalic acid must reduce or eliminate such impurities or convert them to substances inert in the production of polyesters.

Oxidation of paraxylene to crude terephthalic acid is in the presence of a cobalt-manganese catalyst promoted by bromine in an acetic acid-water solution. After liquid-solid separation to obtain the crude terephthalic acid, the mother liquor containing catalyst, acetic acid, 4-carboxybenzaldehyde, color-forming precursors and color bodies and from 1% to 5% crude terephthalic acid, is dewatered. The dewatered oxidation mother liquor can be returned to the oxidation reactor or further treated to recover the catalyst and finally discarded. Return of the dewatered oxidation mother liquor to the oxidation reactor increases the content of 4-CBA, and precursors contributing to color and fluorescence of purified terephthalic acids in the oxidation reactor with consequent decrease in quality of the crude terephthalic acid.

Efforts to selectively hydrogenate impurities and color bodies in the oxidation mother liquor without hydrogenating the terephthalic acid and thus obtain a purified stream suitable for recycle to the oxidation reaction have been typically unsuccessful.

SUMMARY OF INVENTION

It has now been discovered, according to the invention, that oxidation mother liquor of a purity suitable for recycle to the oxidation reactor may be obtained from the impure oxidation mother liquor containing 4-carboxybenzaldehyde, color bodies and other impurities by catalytically hydrogenating the impure oxidation mother liquor containing bromine in the presence of a rhodium catalyst in acid-aqueous liquid phase at elevated temperature and pressure. The 4-carboxybenzaldehyde is converted to p-toluic acid, and color bodies of benzil, fluorenone and anthraquinone structures are converted to saturated compounds, i.e., cyclohexane-type compounds, and oxidized to carbon oxides, without reducing terephthalic acid present.

DETAILS OF THE INVENTION

It has been determined that color bodies in crude terephthalic acid resulting from the oxidation of polyalkyl aromatic compounds are predominantly coupled aromatic compounds such as biphenyl carboxylic acids, benzophenone carboxylic acids, fluorenone carboxylic acids, fluorene carboxylic acids, anthrquinone carboxylic acids, diarylethylene carboxylic acids and fused-ring polycyclic aromatic carboxylic acids.

Hydrogenation of these compounds under suitable conditions to obtain ring-hydrogenation species offers the possibility of oxidizing these compounds to carbon oxides under the conditions of the paraxylene oxidation process. For example, 2,6--di-carboxy-fluorene (DCFe) can be hydrogenated to ring-hydrogenated DCFe which is then burned in the oxidation reaction to carbon oxides. However, DCFe, upon return of the compound to the oxidation reaction is oxidized to 2,6-dicarboxy-fluorenone (DCF), a yellow compound. The reactions are illustrated below.

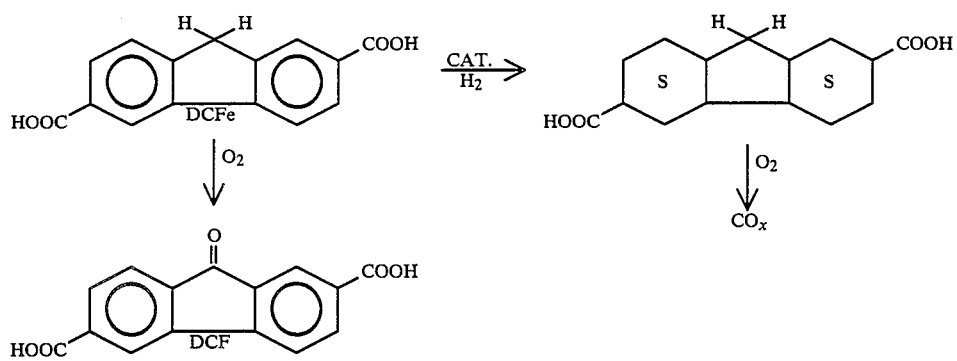

It is therefore desirable to hydrogenate high molecular weight impurities in oxidation mother liquor of the TA process without hydrogenating the TA contained in the oxidation mother liquor. Thereby oxidation mother liquor can be recycled to the TA reactor without impurities which contribute to color and fluorescence. However, because of economic reasons one cannot afford to ring hydrogenate the TA in this stream. Therefore, catalysts have to be highly selective.

I have discovered a process whereby terephthalic acid in oxidation mother liquor containing bromine from the oxidation process of oxidizing paraxylene to terephthalic acid can be recovered by recycling the hydrogenated mother liquor to the oxidation process. The color bodies and impurities which are high molecular weight aromatic compounds are hydrogenated in a bromine-acetic acid solution to cyclohexane-type products which are further oxidized to carbon oxides, i.e., carbon dioxide, etc., upon recycle to the oxidation process. Terephthalic acid in the mother liquor is not hydrogenated and is recovered by return to the oxidation process. Optical quality of crude terephthalic acid is maintained, despite the recycle. Valuable oxidation catalyst in the oxidation mother liquor is recycled without necessity of a separate recovery process.

Essential elements of the invented process are the rhodium on carbon catalyst, the surprising selective catalytic activity of the rhodium catalyst in hydrogenating high molecular weight aromatic compounds in a highly acidic solution containing bromine, and the temperature of the mother liquor stream. Temperature of the stream must be sufficiently high to solubilize all the high molecular weight impurities. Stream temperature can be within the range of from about 250° F. to about 600° F., preferably from about 300° F. to about 400° F. Catalyst comprises rhodium on a support of catalytically active carbon, said rhodium being present in an amount within the range of about 0.5 (wt) % to about 10(wt)%, based in the total dry weight of said catalyst. Preferably the rhodium is present in a range of from about 2 to 5 (wt) %, based on the total dry weight of the catalyst. Catalyst loading of about 0.5 (wt) % or less results in low hydrogenation activity, lower than is economically desirable. Catalyst loading of greater than 10 (wt) % is economically undesirable because of the cost of the catalyst.

The amount of hydrogen supplied under reaction conditions usually is much in excess over the stoichiometric amount required to reduce the characteristically yellow colored impurities present.

Platinum, ruthenium, iridium, and palladium on carbon catalysts have been found to be insufficiently active for hydrogenation of biphenyl compounds in a simulated terephthalic acid oxidation mother liquor. Accordingly, it is essential that rhodium on carbon catalyst be used in the instant invented process.

The present purification process can be carried out in a batch mode as well as a continuous mode. For commercial scale purification of oxidation mother liquor, the continuous mode is preferred.

The rhodium metal component is present on the carrier at a concentration level in the range of about 0.5 (wt)% to about 10 (wt)%, based on the dry weight of the catalyst, i.e., metal plus active carrier and calculated as the active metal. Preferably, the catalyst metal loading is about 2 to 5 (wt) %.

A suitable rhodium-on-carbon catalyst can be obtained, for example, from Engelhard Corporation, Newark, N.J., under the designation "Rhodium on Activated Carbon Granules (Carbon Code CG-5)" and "Rhodium on Activated Carbon Granules (Carbon Code CG-21)." Both of these catalysts have a BET surface area of about 1000 $m^2/g$ and have a particle size of 4×8 mesh, U.S. Sieve Series. Other suitable rhodium-on-carbon catalysts of similar surface area are available from Degussa, Plainfield, N.J., under the designation "5% Rhodium on Activated Carbon Powder, G10 N."

The space velocity reported as weight of mother liquor per weight of catalyst per hour in the purification step is from about 1 $hours^{-1}$ to about 20 $hours^{-1}$, preferably from about 2 $hours^{-1}$ to about 10 $hours^{-1}$.

In summary, the instant invention comprises a process for recovering terephthalic acid from terephthalic acid oxidation mother liquor stream from a paraxylene oxidation reactor, purifying said stream of color bodies and impurities for recycle to said paraxylene oxidation reactor, which process comprises (a) hydrogenating said terephthalic acid oxidation mother liquor stream from said paraxyeene oxidation reactor, said stream comprising acetic acid, oxidation catalyst and bromine promoter, terephthalic acid, color bodies and impurities, in presence of rhodium-on-carbon catalyst, to reduce said color bodies and impurities to cyclohexane-type compounds, (b) recycling said oxidation mother liquor stream to said oxidation reactor, (c) oxidizing said cyclohexane-type compounds to carbon oxides in said oxidation reactor, and (d) recovering terephthalic acid by crystallization and separation from said mother liquor. The catalyst comprises rhodium on a support of catalytically active carbon, said rhodium being present in an amount within the range of about 0.5 (wt) % to about 10 (wt) %, based upon the total dry weight of said catalyst. Preferably, the rhodium is present in an amount of about 2 to 5 (wt) %, based on total dry weight of the catalyst.

The invention has been described with respect to a preferred embodiment thereof. It will be understood, however, by those skilled in the art that modifications may be within the scope of the invention as defined in the claims.

EXAMPLES 1–4

The hydrogenation of diphenic acid (DPA) and 4-carboxybiphenyl (4 CBP) was attempted in these examples. Examples 1–4 were performed in water and in acetic acid and 10 wt% water either without or with 1 wt % HBr to simulate oxidation mother liquor. PTA and two high molecular weight compounds were added. Diphenic acid (2,2′-biphenyl dicarboxylic acid) is a compound which should be difficult to ring hydrogenate because the two rings are not in the same plane. The other compound, 4-carboxybiphenyl, is more representative of typical TA impurities and should be more easily hydrogenated because the rings are planar. All examples were carried out at 300° F. and 400 psi of hydrogen in an autoclave. The solvent in Example 1 was water only. The solvent in Example 2 comprised water and 35 acetic acid. Examples 3 and 4 used a simulated oxidation mother liquor comprising water, acetic acid, hydrogen bromide and terephthalic acid.

In the absence of HBr the two high molecular weight model compounds surprisingly behaved similarly in water, Example 1, and the acetic acid mixture, Example 2, (Table I). In both examples the planar 4-carboxybiphenyl was much more easily reduced than biphenic acid using powdered 5 wt % Pd/C catalyst in suspension. TA was completely reduced in water, but incompletely in the acetic acid mixture. Hardly any reduction at all was noticeable with 5 wt % Pd/C catalyst after addition of one wt % HBr to the acetic acid mixture in Example 3. It was found, however, that a different catalyst—5 wt % Rh on powdered carbon—was able to overcome the apparent deactivation by HBr in Example 4. The 4-carboxybiphenyl concentration was significantly reduced without apparently affecting either TA or biphenic acid (Table I).

The hydrogenation examples were performed in a one gallon titanium autoclave using 0.5 g of palladium on powdered carbon catalyst or 0.5 g of rhodium on carbon catalyst. The mother liquor composition in Examples 3–4 consisted of 90 wt % acetic acid, 9 wt % water and 1 wt % hydrobromic acid. The detailed composition including catalyst was heated to 300° F. at 1000 rpm stirring and at that time a sample was taken for analysis. Then hydrogen was added to increase pressure by 40 psi and additional samples taken every hour for four hours. Analysis showed that neither TA nor biphenic acid was reduced in this process to a large extent.

TABLE 1

| Hydrogenation of Oxidation Mother Liquor Mixtures | | | | | | | | |
|---|---|---|---|---|---|---|---|---|
| Experiment | No. 1 | | No. 2 | | No. 3 | | No. 4 | |
| Catalyst | 5% Pd/C | | 5% Pd/C | | 5% Pd/C | | 5% Rh/C | |
| Amount | 0.5 g | | 0.5 g | | 0.5 g | | 0.5 g | |
| Reactor Content | | | | | | | | |
| D&D Water (ml) | 1000 | | 98 | | 98 | | 98 | |
| Glacial Acetic Acid (ml) | — | | 900 | | 900 | | 900 | |
| 48% HBr (g) | — | | — | | 2 | | 2 | |
| PTA (g) | 10 | | 20 | | 20 | | 20 | |
| Diphenic Acid (DPA) (g) | 1 | | 1 | | 1 | | 1 | |
| 4-Carboxybiphenyl (4-CBP) (g) | 1 | | 1 | | 1 | | 1 | |
| Results (in ppm) | | | | | | | | |
| LC Analysis | DPA | 4-CBP | DPA | 4-CBP | DPA | 4-CBP | DPA | 4-CBP |
| Time, HRS | | | | | | | | |
| 0 | 1000 | 610 | 1030 | 880 | 1020 | 790 | 810 | 580 |
| 1 | 800 | 80 | 840 | 30 | 920 | 750 | 810 | 330 |
| 2 | 710 | 20 | 830 | 10 | 940 | 730 | 810 | 170 |
| 3 | 580 | 10 | 730 | ND | 920 | 720 | 810 | — |
| 4 | 460 | ND | 660 | ND | 890 | 660 | 810 | 90 |
| CHDA* at 4 hr | ~1000 ppm | | ND | | ND | | ND | |

*Cyclohexane Dicarboxylic Acid
Conditions:
300° F.
400 psi H$_2$
1000 rpm stirring
ND - Not detected

EXAMPLES 5–7

The procedure of Example 4 was repeated with catalysts of platinum, ruthenium and iridium. The data in Example 4 wherein the catalyst is rhodium-on-carbon is repeated for comparison. Details are in Table 2.

TABLE 2

| Hydrogenation of Oxidation Mother Liquor Mixtures | | | | |
|---|---|---|---|---|
| Example | No. 4 | No. 5 | No. 6 | No. 7 |
| Catalyst | 5% Rh/C | 5% Pt/C | 5% Ru/C | 1% Ir/C |
| Amount | 0.5 g | 0.5 g | 0.5 g | 2.5 g |
| Reactor Content | | | | |
| D&D Water (ml) | 98 | 98 | 98 | 98 |
| Glacial Acetic Acid (ml) | 900 | 900 | 900 | 900 |
| 48% HBr (g) | 2 | 2 | 2 | 2 |
| PTA (g) | 20 | 20 | 20 | 20 |
| Diphenic Acid (DPA) (g) | 1 | 1 | 1 | 1 |
| 4-Carboxybiphenyl (4-CBP) (g) | 1 | 1 | 1 | 1 |
| Results (in ppm) | | | | |
| LC Analysis | 4-CBP | 4-CBP | 4-CBP | 4-CBP |

TABLE 2-continued

| Hydrogenation of Oxidation Mother Liquor Mixtures | | | | |
|---|---|---|---|---|
| Example | No. 4 | No. 5 | No. 6 | No. 7 |
| Time, HRS | | | | |
| 0 | 580 | 650 | 610 | 600 |
| 1 | 330 | 620 | 570 | 530 |
| 2 | 170 | 590 | 660 | — |
| 3 | — | 520 | 700 | 500 |
| 4 | 90 | 530 | 720 | 530 |
| CHDA* at 4 hr | ND | ND | ND | ND |

*Cyclohexane Dicarboxylic Acid
Conditions:
300° F.
400 psig H$_2$
1000 rpm stirring Platinum, ruthenium and iridium as well as palladium, from example 3, were found to be insufficiently active in a simulated terephthalic acid oxidation mother liquor containing acetic acid and bromine to reduce 4-CBP.

What is claimed is:

1. A process for purifying and recycling an acidic, impure mother liquor from a paraxylene oxidation reactor for production of terephthalic acid, wherein said impure mother liquor contains terephthalic acid and impurities contributing to color and fluorescence of purified terephthalic acid, which process comprises (a) hydrogenating said acidic impure mother liquor stream wherein temperature of said stream is in the range of from about 250° F. to about 600° F. from said paraxylene oxidation reactor, said stream comprising acetic acid, oxidation catalyst and bromine promoter, terephthalic acid, color bodies and impurities, in presence of rhodium-on-carbon catalyst, to reduce said color bodies and impurities to cyclohexame-type compounds,
   (b) recycling said hydrogenated mother liquor stream to said oxidation reactor,
   (c) oxidizing said cyclohexane-type compounds to carbon oxides in said oxidation reactor, and
   (d) recovering oxidation catalysts and terephthalic acid in said mother liquor stream by crystallization from said mother liquor.

2. The process of claim wherein said catalyst comprises rhodium on a support of catalytically active carbon, said rhodium being present in an amount within the range of about 0.5 (wt) % to about 10 (wt) %, based upon the total dry weight of said catalyst.

3. The process of claim wherein said rhodium is present in an amount of about 2 to about 5 (wt) %, based upon the total dry weight of said catalyst.

4. The process of claim wherein temperature of said stream is in the range of about 300° F. to about 400° F.

* * * * *

UNITED STATES PATENT OFFICE
CERTIFICATE OF CORRECTION

Patent No. 4,833,269                         Dated   May 23, 1989

Inventor(s)   Hobe Schroeder

It is certified that error appears in the above-identified patent and that said Letters Patent is hereby corrected as shown below:

| Col. | Line | |
|---|---|---|
| 1 | 8 | "terehhthalic" should read --terephthalic-- |
| 2 | 53 | "anthrquinone" should read --anthraquinone-- |
| 4 | 54 | "paraxyeene" should read --paraxylene-- |
| 5 | 53 | "and 35" should read --and-- |
| 6 | 13 | "40" should read --400-- |
| 8 | 9 | "cyclohexame" should read --cyclohexane-- |
| 8 | 26 | "of" should read --of from-- |

UNITED STATES PATENT OFFICE
CERTIFICATE OF CORRECTION

Patent No. 4,833,269      Dated May 23, 1989

Inventor(s) Hobe Schroeder

It is certified that error appears in the above-identified patent and that said Letters Patent is hereby corrected as shown below:

| Col. | Line | |
|---|---|---|
| 8 | 17 | "claim" should read --Claim 1-- |
| 8 | 22 | "claim" should read --Claim 2-- |
| 8 | 25 | "claim" should read --Claim 1-- |

Signed and Sealed this

Thirtieth Day of January, 1990

Attest:

JEFFREY M. SAMUELS

*Attesting Officer*     *Acting Commissioner of Patents and Trademarks*